US00PP19969P3

(12) United States Plant Patent
Lim

(10) Patent No.: US PP19,969 P3
(45) Date of Patent: Apr. 28, 2009

(54) GRANDIFLORA ROSE PLANT NAMED 'BAINCE'

(50) Latin Name: *Rosa hybrida*
Varietal Denomination: BAInce

(75) Inventor: Peter P. Lim, McMinnville, OR (US)

(73) Assignee: Bailey Nurseries, Inc., Newport, MN (US)

( * ) Notice: Subject to any disclaimer, the term of this patent is extended or adjusted under 35 U.S.C. 154(b) by 151 days.

(21) Appl. No.: 11/818,369

(22) Filed: Jun. 14, 2007

(65) Prior Publication Data

US 2008/0313780 P1 Dec. 18, 2008

(51) Int. Cl.
*A01H 5/00* (2006.01)

(52) U.S. Cl. ..... Plt./136

(58) Field of Classification Search ..... Plt./136
See application file for complete search history.

*Primary Examiner*—Kent L Bell
(74) *Attorney, Agent, or Firm*—Penny J. Aguirre

(57) ABSTRACT

A new cultivar of grandiflora rose, *Rosa* 'BAInce', characterized by its strongly fragrant fully double, salmon pink flowers held on sturdy stems, its upright plant habit and its everblooming habit. The new variety has medium green foliage that is resistant to black spot and powdery mildew, is a vigorous grower, is readily propagated on its own roots and is hardy in U.S.D.A. Zones 5 to 9.

2 Drawing Sheets

Botanical classification: *Rosa hybrida.*
Variety denomination: 'BAInce'.

BACKGROUND OF THE INVENTION

The present invention relates to a new and distinct cultivar of *Rosa hybrida.* The new cultivar will be referred to hereafter by its cultivar name, 'BAInce'. 'BAInce' is a grandiflora rose suitable for landscape plantings.

The new cultivar of shrub rose is a selection from a controlled breeding program conducted by the inventor in Yamhill, Oreg. with a focus to create cultivars of roses with greater winter hardiness and improvements in disease resistance combined with good flower quality.

The new variety of shrub rose, 'BAInce', designated as seedling No 91G716 was selected among seedlings derived from a cross made in Yamhill, Oreg. in 1991 between the female parent, 'Earth Song' (not patented) and the male parent, 'TWOadvance' (U.S. Plant Pat. No. 7,978). 'BAInce' was selected as unique and budded onto understock in August 1992 and reselected by the inventors for its distinct characteristics in 2000.

The new cultivar has been asexually propagated by rooting of softwood cuttings from a plant grown its own roots in Yamhill, Oreg. Asexual propagation determined that the characteristics of this cultivar are stable and are reproduced true to type in successive generations.

SUMMARY OF THE INVENTION

The following traits have been repeatedly observed and represent the characteristics of the new rose as observed for a period of six years in Yamhill, Oreg. and evaluated further at several other test sites in the U.S. These attributes in combination distinguish 'BAInce' as a unique cultivar of grandiflora rose.

1. 'BAInce' exhibits fully double salmon pink colored flowers that emerge from hybrid tea-shaped buds that are coral colored with a yellow base. Classified as apricot by American Rose Society standards.
2. 'BAInce' exhibits an upright plant habit.
3. 'BAInce' exhibits medium green foliage.
4. 'BAInce' is everblooming.
5. 'BAInce' has shown excellent resistance to rose blackspot (*Diplocarpon rosae*) and powdery mildew (*Sphaerotheca pannosa* var. *rosa*).
6. 'BAInce' is very fragrant.
7. 'BAInce' exhibits sturdy canes.
8. 'BAInce' is hardy in U.S.D.A. Zones 5 to 9.
9. 'BAInce' is a vigorous grower and readily propagated by softwood cuttings and grown on its own roots.

The new cultivar of shrub rose can be readily distinguished from its parents and other cultivars. The female parent, 'Earth Song', has deep pink flowers with moderate fragrance and dark green glossy foliage. The male parent, 'TWOadvance', has similar colored flowers, however it is a shrub rose with semi-double flowers. The cultivars 'Prairie Sunrise' (not patented) and 'BAIcent' (U.S. plant patent pending) are the closest comparison roses. They both have similarity to 'BAInce' in flower color and have upright plant habits, however they are both taller in height and recurrent bloomers. They also differ in that 'Prairie Sunrise' is a shrub rose with fuller flowers and apricot-red colored buds while 'BAIcent' has double flowers that are not as full, dark apricot colored buds, and smaller flowers.

BRIEF DESCRIPTION OF THE DRAWING

The accompanying colored photographs illustrate the overall appearance and distinct characteristics of the new shrub rose, 'BAInce', as grown outdoors in trial blocks and containers in St. Paul, Minn. and Yamhill, Oreg. The photographs were taken of two to three year-old plants grown on their own roots.

Figure 1:
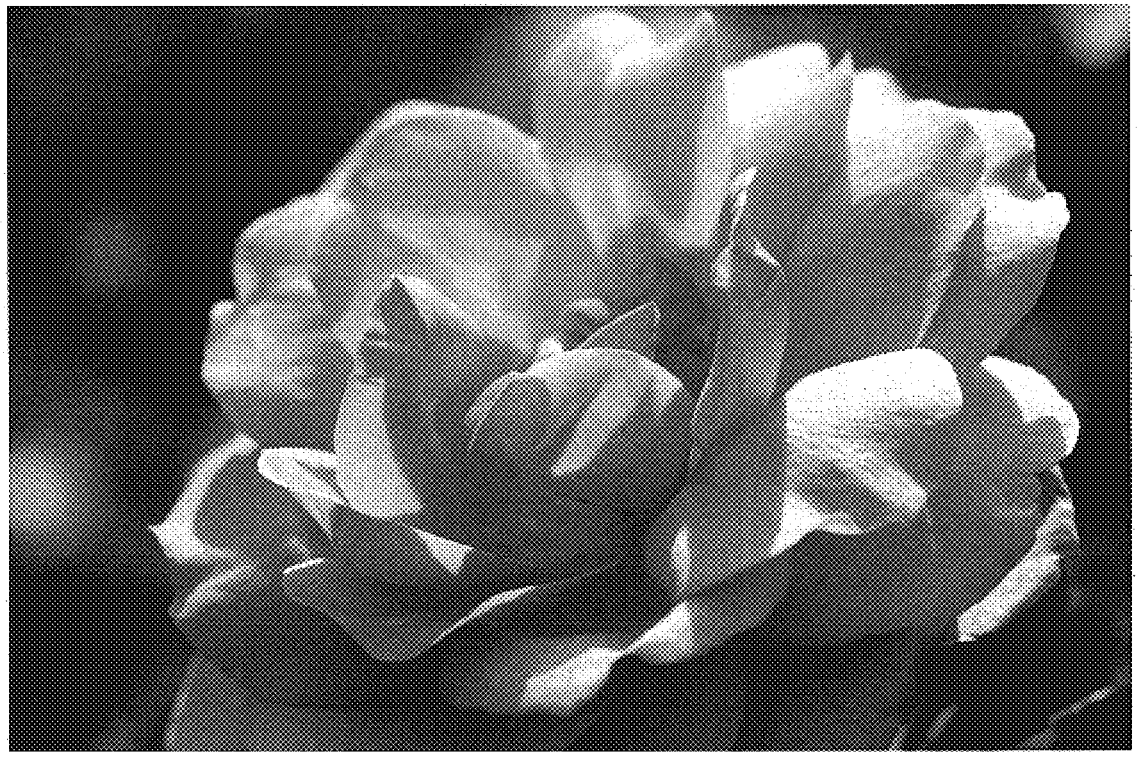
FIG. 1 provides a view of a fully open flower, FIG. 2 provides a view of a flower bud just prior to opening and FIG. 3 provides a view of a cluster of partially open flowers.
Figure 2:
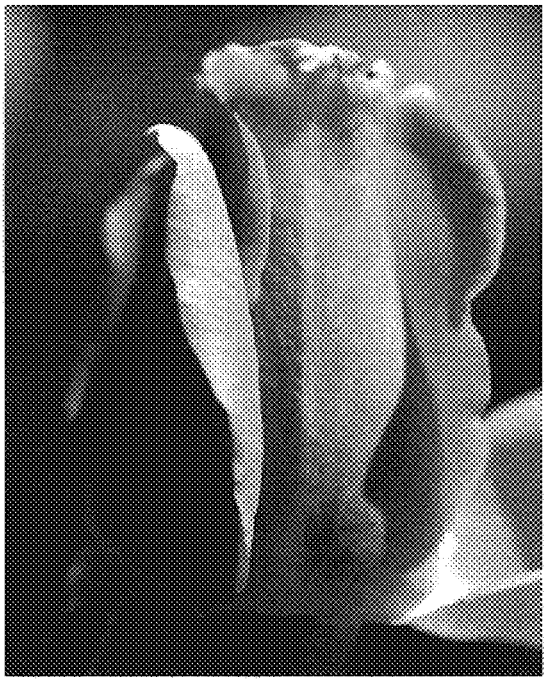
Figure 3:
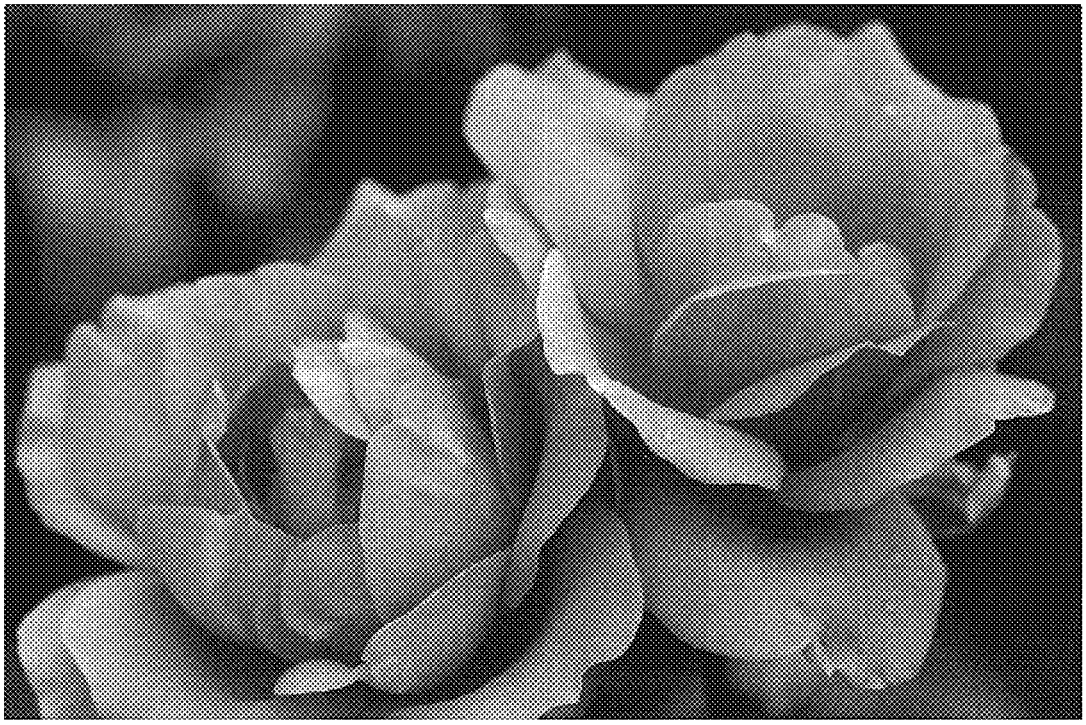

The colors in the photographs are as close as possible with digital photography techniques available, the color values cited in the detailed botanical description accurately describe the colors of the new grandliflora rose.

DETAILED BOTANICAL DESCRIPTION

The following is a detailed description of the new cultivar as observed on two year-old container plants as grown in a 2 gallon container and six year-old field grown plants as grown outdoors in Yamhill, Oreg. and St. Paul, Minn. The phenotype of the new cultivar may vary with variations in environmental, climatic, and cultural conditions, as it has not been tested under all possible environmental conditions. The color determination is in accordance with the R.H.S. Colour Chart of The Royal Horticultural Society, London, England, except where general color terms of ordinary dictionary significance are used.

General description:

*Botanical classification.*—*Rosa hybrida* 'BAInce'.

*Parentage.*—Seed parent *Rosa* 'Earth Song', pollen parent *Rosa* 'Twoadvance'.

*Blooming habit.*—Everblooming throughout the growing season.

*Plant habit.*—Upright, nearly oval.

*Plant height.*—Reaches 60 to 125 cm in height and 60 to 125 cm in spread.

*Cold hardiness.*—U.S.D.A. Zone 5 to 9.

*Diseases and pests.*—High degree of resistance observed to rose blackspot (*Diplocarpon rosae*) and powdery mildew (*Sphaerotheca pannosa* var. *rosa*).

*Propagation.*—Softwood stem cuttings, own roots.

*Growth.*—Vigorous.

Branch description:

*Stem color.*—Young; between 144A to 144B, mature; 138B variably suffused with N77A, mature wood; 197A with areas of 138B showing through ridges.

*Stem surface.*—Young; glabrous, mature; slightly glaucous, adult wood; mostly glabrous with bark-like ridges.

*Stem strength.*—Sturdy.

*Stem size.*—Average of 4.5 mm in width, laterals average about 21 cm in length.

*Branching.*—Average of 6 lateral stems with 1 to 3 sublateral stems per lateral stem.

*Thorns.*—Narrowly triangular in shape, slightly curved downward, oval base, average of 4 per 5 cm in number, average of 4 mm in length with a base 3 mm in length and 2 mm in width, N77B in color.

Foliage description:

*Leaves.*—Division is odd-pinnate, arrangement is alternate, average of 9 cm in length and 7 cm in width, internode length is an average of 2 cm.

*Leaflets.*—5 to 7 (typically 5), elliptic to oval in shape, rounded to cuneate base, acute apex, serrated margins, glabrous on upper surface and finely pubescent on lower surface, average of 3.5 cm in length and 2.3 cm in width (lateral leaves), color: young leaves upper surface; 144A, young leaves lower surface: 144A lightly suffused with 59B, mature leaves upper surface; 139A with very edge of margins 187A, mature leaves lower surface; 138A suffused with 187C, pinnately veined only conspicuous on midrib; 187A in color.

*Rachis.*—Average of 4.5 cm in length and 1.2 mm in diameter, color of upper surface 138A variably suffused with 187A, color of lower surface 144B to 144D lightly suffused with 187C, surface is glabrous with a few small prickles on margin and underside and small thorns on underside (about 2 per rachis) and a tomentose in center of ridge of upper surface.

*Stipules.*—Parallel with auricle facing outward, adnate to petiole, average of 1.2 mm in length and 1 cm in width, color on upper side is 137B with 144D on middle ridge, color of lower surface is 137B, surface is glabrous on upper surface with prickles on lower surface.

*Petioles.*—Average of 1.5 cm in length and 1.2 mm in diameter, 137A with center 187C, color of upper surface 138A variably suffused with 187A, color of lower surface 144B to 144D lightly suffused with 187C, surface is glabrous with a few small prickles on margin and underside and small thorns on underside (about 2 per rachis) and a tomentose in center of ridge of upper surface.

Inflorescence description:

*Inflorescence type.*—Single terminals and clusters (typically 2) fully double, rounded formed flowers.

*Flower number.*—Average of 1.5 per lateral and sublateral stem, about 9 per 2 gallon plant.

*Flower fragrance.*—Strong rose scent.

*Flower longevity.*—About 3 to 5 days, depending on temperature and sunlight exposure.

*Flower type.*—Full (fully double).

*Flower size.*—7.5 to 10 cm in diameter and an average of 5.5 cm in depth.

*Peduncles.*—Stiff, average of 5 cm in length and 2.7 mm in diameter, color is 139A lightly suffused with N77A, surface is glossy with some sparse hairs and prickles.

*Bracts.*—Not observed.

*Flower buds.*—Ovate in shape (hybrid tea-shaped), medium in size with an average of 3.2 cm in length and 2.3 cm in width prior to opening, color 33A when first showing color, changing to 33B blended with some 11B with a base of 11B.

*Sepals.*—5 broadly lanceolate in shape, margin is entire and tomentose with foliaceous appendages on 2 to 3, color of upper surface is 138A to 138B, color of lower surface is 138A, upper surface is tomentose, lower surface is pubescent, average of 2.2 cm in length and 1.1 cm in width, apex is apiculate to changing to leaf-like, base is truncate, aspect is upright in tight bud stage changing to horizontal and finally reflexed when flower opens.

*Petals.*—Average of 35, drop readily and cleanly, broadly obovate in shape and curled under on sides and margins, upper and lower surface is glabrous and satiny, margin is entire with variable notches, cuneate base, apex is rounded to notched, average of 5 cm in length and 3.5 cm in width (inner petals smaller), color: upper surface; 48C, opening flowers lower surface; 48C blended with some 11C, fully open flowers upper and lower surface; blend of 62A to 62D with spots near apex of 61D on upper surface, fading flowers upper and lower surface; 62C to 62D, base petal spot; 11A surrounded by a lighter area of 11C to 11D.

*Receptacle.*—Average of 7 mm in diameter and 1 cm in depth when flower is fully open, urn shaped, glabrous and satiny, color is 138A.

*Pistils.*—About 30, stigma is an average of 0.3 mm in depth and 1 mm width and 162B in color, style is an average of 7 mm in length and 154C in color near base and 58A near apex, ovary is about 2.5 mm in length and 1 mm in width and 155A in color with white long hairs.

*Stamens.*—About 80, filaments are about 9 mm in length and 154C in color, anthers are an average of 2.5 mm in length, an average of 9 mm in width and 154C in color, pollen is moderate in quantity and 166A in color.

*Hips.*—Round in shape and yellow-orange in color.

I claim:

1. A new and distinct cultivar of shrub rose plant named 'BAInce' as herein illustrated and described.

* * * * *